United States Patent [19]
Benedetti

[11] Patent Number: 6,050,413
[45] Date of Patent: Apr. 18, 2000

[54] PLASTER SYSTEM

[75] Inventor: Giovanni Benedetti, Ayrshire, United Kingdom

[73] Assignee: Wallace Cameron & Company Limited, Glasgow, United Kingdom

[21] Appl. No.: 09/287,496

[22] Filed: Apr. 6, 1999

[30] Foreign Application Priority Data

Apr. 6, 1998 [GB] United Kingdom .................... 9807281

[51] Int. Cl.[7] ..................................... A61B 17/06
[52] U.S. Cl. ........................... 206/440; 206/477; 206/807
[58] Field of Search ..................................... 206/440, 441, 206/570, 438, 803, 807, 477, 483; 248/551, 553, 316.7

[56] References Cited

U.S. PATENT DOCUMENTS

| | | | |
|---|---|---|---|
| 4,194,624 | 3/1980 | Spiegelberg | 206/441 |
| 4,993,586 | 2/1991 | Taulbee et al. | 206/441 |
| 5,470,323 | 11/1995 | Smith et al. | 206/441 |
| 5,511,689 | 4/1996 | Frank | 206/440 |

*Primary Examiner*—Paul T. Sewell
*Assistant Examiner*—J. Mohandesi
*Attorney, Agent, or Firm*—Ratner & Prestia

[57] ABSTRACT

A pilfer-proof device for storing individually wrapped sticking plasters. The device comprises a support and at least one cassette holding securely a plurality of wrapped plasters. The cassette is removably attached to the support by a locking clip. The device further comprises a locking bar being able to lock said cassette on said support into a non-removable position. The security bar is moveable with respect to the support between a first position wherein said locking means cooperates with said cassette to lock said cassette in said non-removable position and a second position wherein said locking clip does not lock said cassette. Further, the support is further provided with a lock to restrict movement of the bar from the first position.

14 Claims, 4 Drawing Sheets

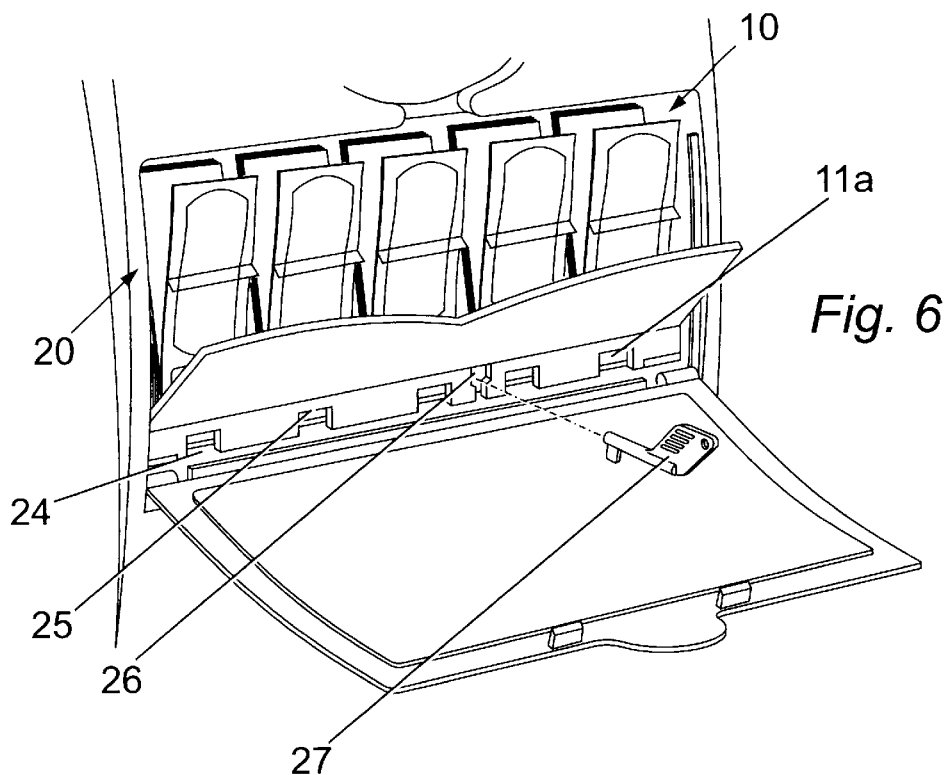
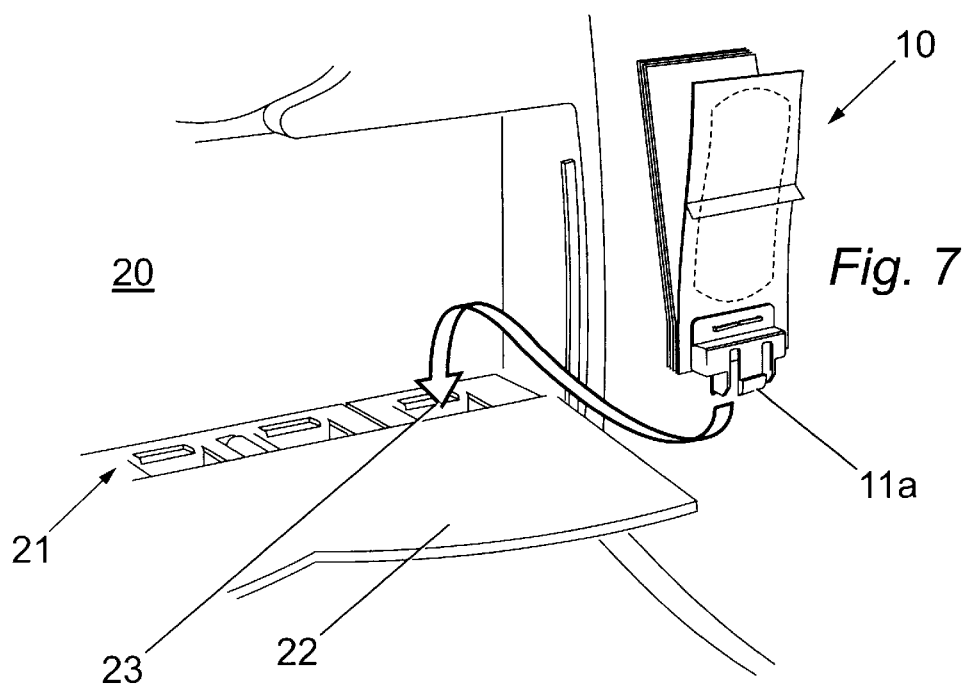

PLASTER SYSTEM

FIELD OF THE INVENTION

The present invention relates to an apparatus for holding and dispensing sticking plasters.

BACKGROUND OF THE INVENTION

Sticking plasters, which comprise an adhesive backing sheet and a small absorbent dressing (both protected by a cover sheet until required) are very well known and are widely used to protect minor flesh wounds from dirt and contamination. Sticking plasters are commonly termed "plasters" and are available in a range of sizes and with a variety of backing sheet types and colours.

It is common in most workplaces for the management to provide a small supply of plasters for use by employees. Typically the plasters supplied will be suited to the nature of the work conducted. For example, in food handling or medical situations it is desirable for any plaster worn by an operator to have a clearly visible (eg bright blue) backing sheet. The clear visibility of the plaster helps to avoid an inadvertently displaced plaster contaminating the food or medical materials being prepared or handled.

The minor nature of the wound to be protected by the plaster means that medical consultation concerning the wound itself or concerning the need for a plaster is unnecessary, and also that the number of incidents requiring the application of a plaster are relatively high. Generally, therefore, the limited supply of plasters provided will be reasonably accessible, with the injured person themselves deciding on the need for a plaster, collecting a suitably sized and shaped plaster and applying it to the affected area. However, the provision of a limited but generally accessible supply of plasters, by an employer, in a school or otherwise, is unfortunately open to abuse. This arrangement leaves open the possibility that individuals can remove a substantial amount of the whole supply of plasters for their own use in the future. Continual replenishment of stolen plasters would clearly be an unacceptable expense. To circumvent this problem "pilfer-proof" systems have been devised in which sticking plasters can only be removed one at a time and without at least some of their wrapping. Thus plasters continue to be available to those in genuine need, but the removal of multiple plasters for use at a later date becomes impractical.

One such system, illustrated in FIG. 1, is sold under the trademark SALVEQUICK. The system consists of a cardboard folder or booklet 1 which is fastened by staples 4, along the bottom edge to retain a number of wrapped plasters 2. Typically, the cardboard booklet 1 will be wide enough to contain two or three plasters 2 in each row, and for example may have 18 such rows (for clarity only the first row of plasters is shown). The booklet 1 is designed to slot into a compartment of a wall mounted first aid cabinet (not shown). The front cover 3 of the booklet 1, which is shorter than the back cover to expose and permit access to the plasters 2, will in use be located behind a lip at the front edge of the compartment and the lip acts to prevent the whole booklet from being removed. To further ensure that the booklet is retained, four equally spaced vertical cuts are present in the cover 3, the cuts extending from the top edge down substantially the whole of the cover 3 so that it consists of four finger portions 9. To remove the booklet 1, it would be necessary to simultaneously depress all four fingers 9 past the lip of the compartment edge. The front of the compartment has a number of apertures located therein, the apertures being close to the top edge of the compartment and at varying distances therefrom. A key having projections corresponding to the aperture positions and of a length sufficient to pass through the apertures and depress each finger 9 past the lip is provided so that used booklets 1 can be removed and replaced.

As illustrated in FIG. 1 each plaster 5 contained within the SALVEQUICK system is protected by two partial and overlapping wrappers 7, 8. The top wrapper 7 is however only present in plasters for the UK market. This top wrapper 7, when present, may conveniently be transparent to display the plaster 5, and may extend down approximately one third of the length of plaster 5. The lower wrapper 8 protects the remaining portion of the plaster 5 and extends below the bottom of the plaster 5 into the fold of the booklet 1. The lower wrapper 8 is firmly attached to the booklet 1 by staples 4. The top edge of the lower wrapper 8 and the bottom edge of the top wrapper 7 are glued together, the glued edges of each wrapper projecting outwardly from the sticking plaster 5 at each side thereof to form tabs 6. To remove the plaster 5, the top portion thereof is grasped firmly (via top wrapper 7, if present) and pulled upwardly. The plaster 5, which may be partially protected by the top wrapper 7, is then dislodged from the lower wrapper 8, as the two wrappers 7, 8 pull part along each tab 6. The lower portion of the removed sticking plaster 5 is exposed and can be applied immediately. The lower wrapper 8 remains in the booklet 1. Plaster 5 can then be fully applied, if necessary following removal of the top wrapper 7, which can be easily accomplished by pulling on the exposed tab 6 (which was previously glued to the lower wrapper 8). Whilst the plaster 5 is ready for application as soon as it is removed from the booklet, the SALVEQUICK system does not provide sterile plasters.

STATEMENT OF THE INVENTION

The present invention provides an alternative pilfer-proof system for storing and dispensing sticking plasters.

The pilfer-proof device for storing individually wrapped sticking plasters according to the invention comprises:
- a support;
- at least one cassette having holding means securely attaching a plurality of wrapped plasters, the cassette being removably attached to the support by attachment means; and
- a locking bar having locking means to lock the cassette into a non-removable position on the support, the bar being moveable with respect to the support between a first position wherein the locking means cooperates with said cassette or said support to lock said cassette in said non-removable position and a second position wherein said locking means does not lock said cassette.

Further, the support is further provided with means to restrict movement of the bar from the first position.

It is preferred that the locking bar is designed to cooperate with the cassette so that the cassette is either in a "locked" position (ie during normal use) or is in a "removable" or unlocked position (ie to allow cassettes holding only used plasters to be removed and replaced).

The locking bar may be positioned in a recess or groove on the support or may be retained thereon by projections or loops forming part of, or attached to, the support.

Means to restrict movement of the bar from the first position may comprise a keyhole which engages with a rotating key to produce displacement of the locking bar from the first position to the second position. These means to restrict movement of the locking bar from the first position may comprise a casing provided on said support and which protects said bar from movement due to direct human access. By "direct human access" it is meant that a person cannot with only his/her bare hands easily move the locking bar to the unlocked position. The device of the invention is not designed to be a 100% security proof system but a good deterrent against pilferers.

Optionally the locking bar is retained within a casing into which the cassette(s) is/are inserted.

Optionally, the locking bar is located along the floor of a compartment which is to hold the sticking plasters. Alternatively, the surface may be in the form of a platform (ie mounted horizontally) or a plaque (ie mounted vertically). In one embodiment the compartment itself is located in the door of a first aid kit.

Optionally multiple plaster cassettes are located side by side along the locking bar and are all locked in a non-removable position on said support when the locking bar is in said first position. The number of plaster cassettes may range from 2 to 10, preferably 4, 5 or 6. Desirably the locking bar has two positions, so that all the cassettes located on the locking bar switch from the "locked" to the "removable" state (and vice versa) simultaneously.

It may therefore be advantageous for the removable cassette(s) to remain correctly positioned until positively dislodged as this would enable only selected cassettes to be replaced without requiring the remainder to be dislodged and then reinserted. It is thus preferred that the attachment means of each cassette comprises a locking clip which cooperates with a corresponding lip provided on the support.

A preferred option is for the removal of a cassette to require two actions, first the transition of the cassette from a locked to a removable state (for example by sideward displacement of the locking bar) and second for the bottom of the locking clip to be depressed which will disengage it from a lip before the cassette can be lifted out of the device.

Advantageously the locking bar includes locking projections or tabs spaced along its length. When the attachment means of the cassette is a locking clip, the projection may advantageously be present behind the clip. The cassette is therefore "locked" as the clip cannot be depressed past the lip on the support. Following sideways movement of the locking bar the tab/projection is displaced sideways and the cassette becomes "removable" and the clip may be depressed past the retaining lip.

In one embodiment the locking bar is positioned within a casing, the casing having a lip which engages with a portion of the clip. Thus, a cassette located on the locking bar is positioned such that the clip is behind this lip. To remove a cassette it is necessary to move the locking bar sideways, such that the cassette becomes removable and then to depress the clip in order to push it over the lip of the casing. Depressing the clip when the locking bar is in the locked position does not permit removal; a tab on the locking bar prevents the clip from being pushed sufficiently far to overcome the lip.

Optionally, the locking bar may include guiding tongues which accurately locate the locking bar itself and/or the cassette.

Optionally, the locking bar may include a keyhole which engages with a rotating key to produce the desired sideward displacement.

The plasters may be held in the cassette by a staple or other fastening means which passes through the cassette and each bottom edge of the plaster wrappers. For ease of removability, the plaster itself should not be attached to the cassette, other than via the wrapper. The plasters may alternatively be held in the clip by gluing the bottom edge of the wrapper therein.

The cassette support and locking bar may be made of plastic or other suitable material.

The size and width of the cassette may be altered to suit the plasters held thereby. The cassette may hold a single size and/or type of plaster. Alternatively a range of sizes and/or types of plasters may be held by a single cassette.

Preferably the plasters are sterile.

Generally, the plasters have a backing sheet provided with an adhesive layer provided with an absorbent dressing thereon. The adhesive face of the backing sheet and the dressing will desirably be protected by a cover sheet (which may be present as two partially overlapping separate sheets), the whole being protected by a wrapper. These wrappers may comprise at least two portions attached together.

In one embodiment at least one of these wrapper portions is not secured by the holding means of the plaster cassette. It is preferred the wrapper consists of a lower wrapper portion, the bottom edge of which is held firmly in the cassette, and an upper wrapper portion. The two wrapper portions may meet in approximately the middle of the plaster and may be glued together at each side to form a tab. By pulling upwardly on the upper wrapper portion the plaster is displaced from the lower wrapper portion and the lower and upper wrapper portions part company along the glued tabs. Optionally the lower cover sheet is automatically removed as the plaster is displaced upwards (for example by gluing the edge of the cover sheet to the inside of the lower wrapper portion) and may be retained in the lower wrapper portion. The upper wrapper portion may then be removed from the plaster. Optionally the upper cover sheet is automatically removed as the plaster is applied (for example by gluing the lower edge of the upper cover sheet to the inside of the upper wrapper portion).

A further object of the invention is a plaster cassette to be used in a pilfer-proof device as above described. Such cassette comprises holding means which securely attach a plurality of wrapped plasters. The cassette is sized and shaped to be removably attached to the support of the pilfer-proof device by attachment means. Those attachment means are able to be locked in a non-removable position whilst attached to the support by a locking bar which has locking means to lock said cassette in a non-removable position on the support. This bar is moveable with respect to the support between a first position wherein said locking means cooperates with the cassette or the support to lock the cassette in a non-removable position and a second position wherein said locking means does not lock said cassette.

It is preferred that the attachment means of the cassette comprises a locking clip which cooperates with a corresponding lip provided on the support.

Generally, each cassette would comprise a multiplicity of plasters, normally 2 to 20, more usually 6 to 15, and for example 10 or 12 plasters.

Further, the present invention provides a first aid kit having a pilfer-proof plaster system as described above.

The present invention will now be further described with reference to the, non-limiting, drawings.

BRIEF DESCRIPTION OF THE DRAWINGS

FIG. 6 schematically illustrates a pilfer-proof plaster system according to the invention containing five plaster cassettes of the type shown in FIG. 2.

FIG. 7 shows the casing and compartment of the empty pilfer-proof plaster system of FIG. 6 and indicates the insertion of the first plaster cassette therein.

DETAILED DESCRIPTION OF PREFERRED EMBODIMENTS OF THE INVENTION

Figure 1:
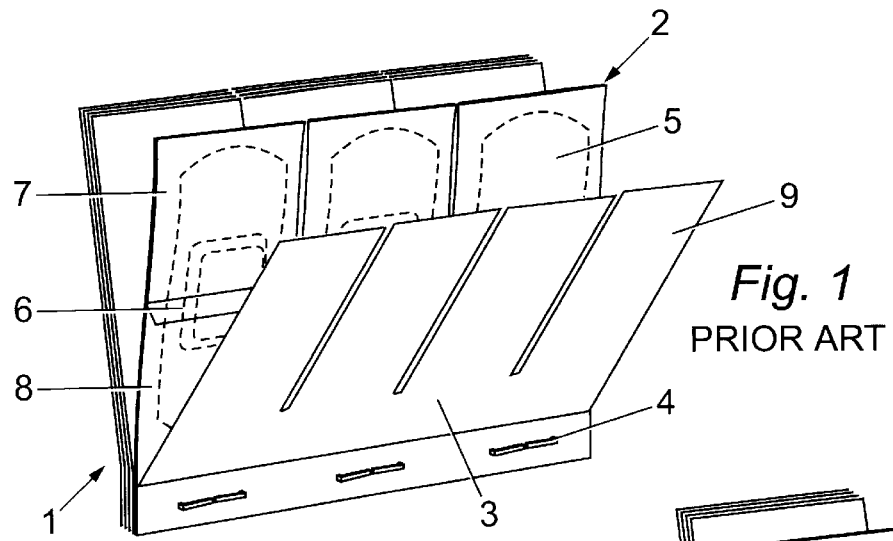
FIG. 1 schematically illustrates a plastic cassette for a known pilfer-proof plaster system.
Figure 2:
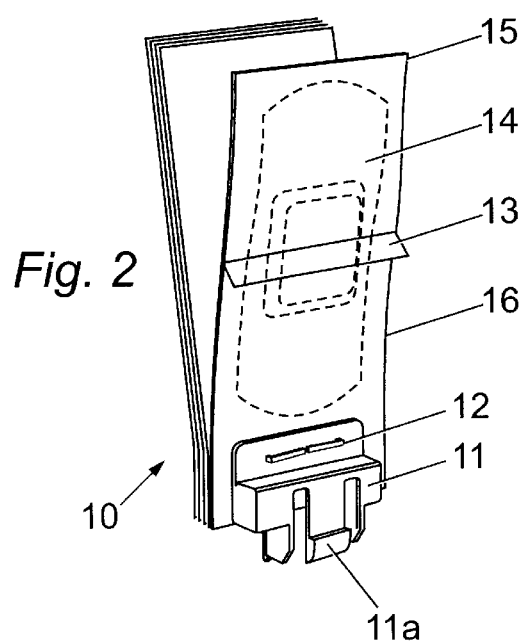
FIG. 2 is a schematic illustration of a plaster cassette according to the present invention show in detail the clip and the first plaster, the remaining plasters being shown in the outline only for clarity.
Figure 3:
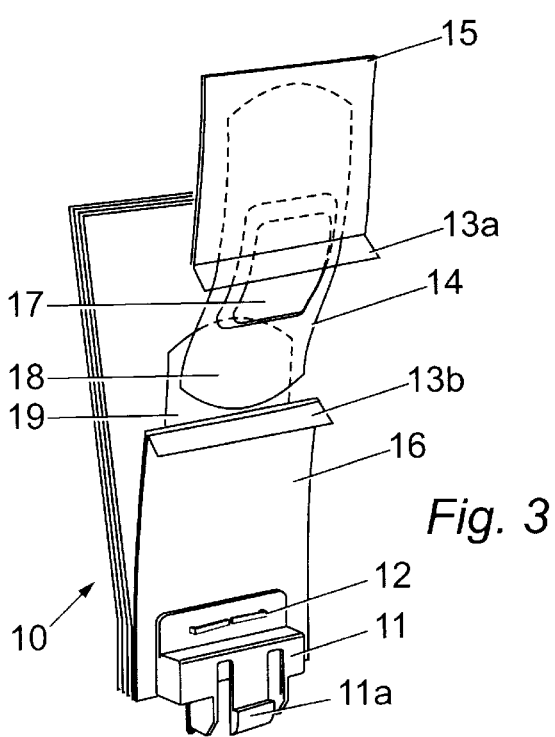
FIG. 3 illustrates the plaster cassette of FIG. 2, in which the first plaster has been withdrawn upwardly in preparation for immediate use.

In more detail, FIG. 2 illustrates a plaster cassette 10 according to the invention. The cassette 10 is comprised of a plastic body 11 which hold a number (usually about 10) of wrapped plasters 14. In FIGS. 2 and 3 only the front plaster is shown in detail for clarity. Plaster 14 consists of an adhesive backing sheet 18 and an absorbent dressing 17 located approximately centrally thereon. The adhesive backing sheet 18 is protected by two cover sheets 19, 20 (see FIGS. 3 and 5) and by upper and lower wrappers 15, 16. Each wrapper 15, 16 consists of two sheets of suitable protective material sealed thereof around the edges. The bottom edge of the upper wrapper 15 and the top edge of the lower wrapper 16 project upwardly to form tabs 13a, 13b. Each of the wrapped plasters 14 is firmly attached to body 11 by means of staple 12 which passes through the front cover of body 11, through the bottom part of the lower wrapper 16 for each plaster 14 and through the back of body 11.

Figure 4:
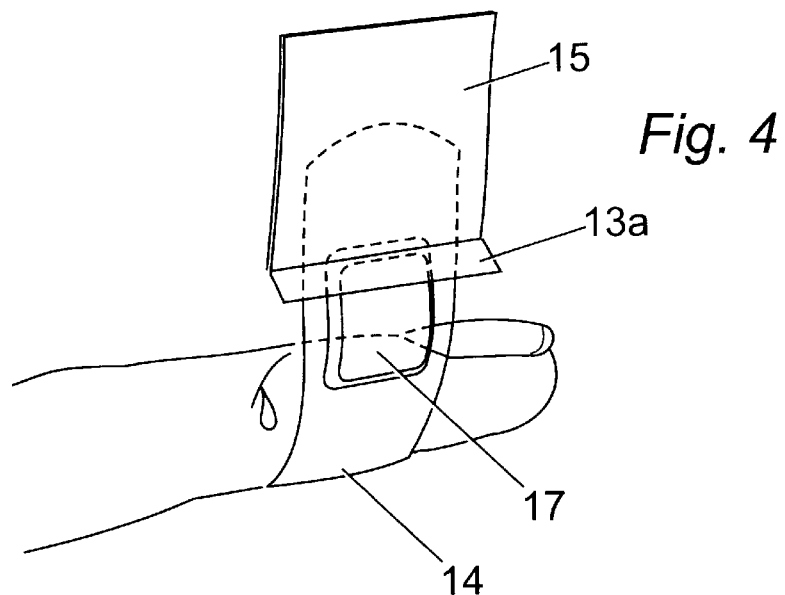
FIG. 4 shows the removed plaster of FIG. 3 being applied to a wounded area on a finger.

When a plaster is required the top portion of plaster 14 is gripped through upper wrapper 15 and pulled upwardly. The remainder of cassette 10, including lower wrapper 16, is attached to the pilfer-proof plaster system and remains essentially stationary. The upward movement of plaster 14 and upper wrapper 15 causes tabs 13a and 13b (which are normally simply glued together) on each side of the wrappers 15, 16 to part company, enabling plaster 14, held via upper wrapper 15, to be lifted free of cassette 10 (FIG. 3). As shown in FIG. 3 the lower portion of the adhesive surface 18 of plaster 14 may be protected during storage by a lower cover sheet 19. Since the plaster 14 is intended for imminent use, it is desirable for the lower cover sheet 19 to be automatically peeled away from adhesive surface 18 as plaster 14 is removed from the cassette 10. This can be achieved by gluing a portion of the lower cover sheet 19 to an inner surface of lower wrapper 16 or to lower tab 13b. Thus, when plaster 14 is pulled out of cassette 10 the lower cover sheet 19 remains attached to cassette 10 and approximately half of adhesive sheet 18 is no longer protected. Plaster 14 is thus suitable for immediate use only. FIG. 4 illustrates plaster 14, removed from cassette 10 of FIG. 3, being applied to an injured finger. The only action required to apply plaster 14 is for adhesive surface 18 to be firmly pressed onto the surface of uninjured skin such that adhesive dressing 17 is positioned over the injured part. In order to apply the remainder of the plaster 14, upper wrapper 15 can be pulled away from plaster 14, whilst the remaining portion of plaster 14 is simultaneously pressed onto the body surface as required (see FIG. 4).

Figure 5:
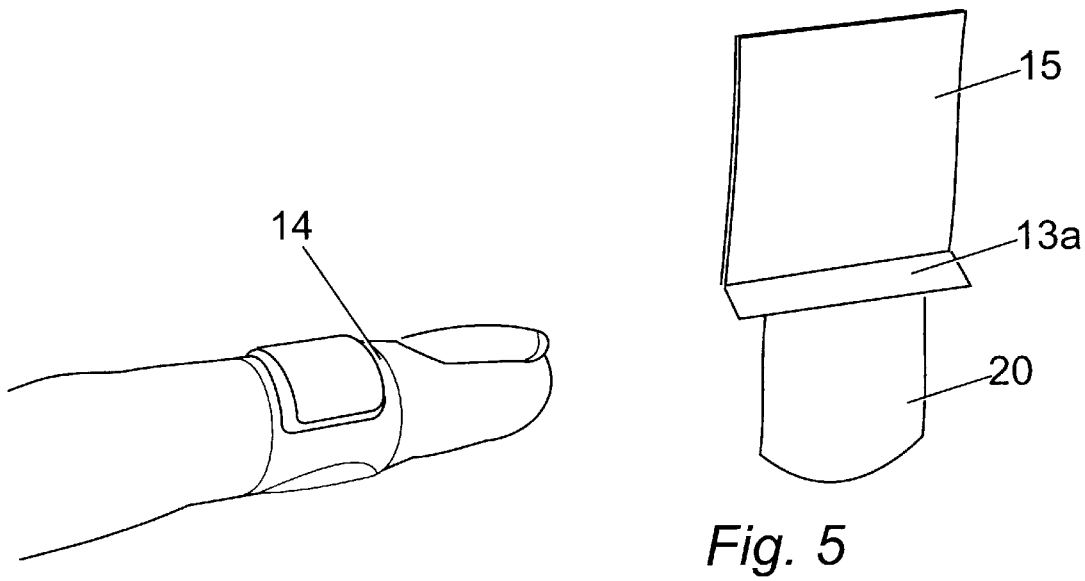
FIG. 5 shows the plaster of FIG. 4 fully applied to the affected area on the finger and the empty plaster wrapper.

The upper portion of plaster 14 as illustrated in FIG. 5 also has an upper cover sheet 20 protecting the upper portion of adhesive backing 18. As upper wrapper 15 is pulled away from plaster 14 (as shown in FIG. 4) the upper cover sheet 20 is automatically removed from the adhesive backing 18. Since a portion of upper cover sheet 20 is attached to an inner surface of upper wrapper 15 or upper tab 13a. FIG. 5 illustrates plaster 14 fully applied to the finger as shown in FIG. 4, together with the empty upper wrapper 15 and inverted upper cover sheet 20 which can then be discarded.

FIG. 6 illustrates a pilfer-proof plaster system according to the invention containing 5 plaster cassettes 10 located in compartment 20. The locking bar, which is not apparent from the FIG. 6, is located behind casing 21 (see FIG. 7). As illustrated in FIG. 7 a plaster cassette 10 is located in casing 21 by insertion through aperture 23. Locking clip 11a of cassette 10 (see also FIG. 2) locates into aperture 24 (see FIG. 6) and cannot be depressed through aperture 24 whilst locking bar 28 remains in its first position. Locking bar 28 may be displaced sideways when key 27 is located in keyhole 26 and rotated, such that the locking bar 28 is urged from its first position to its second position. In its second position the locking bar 28 does not prevent projection 11a from being depressed through aperture 24, enabling cassette 10 to be removed.

Figure 8:
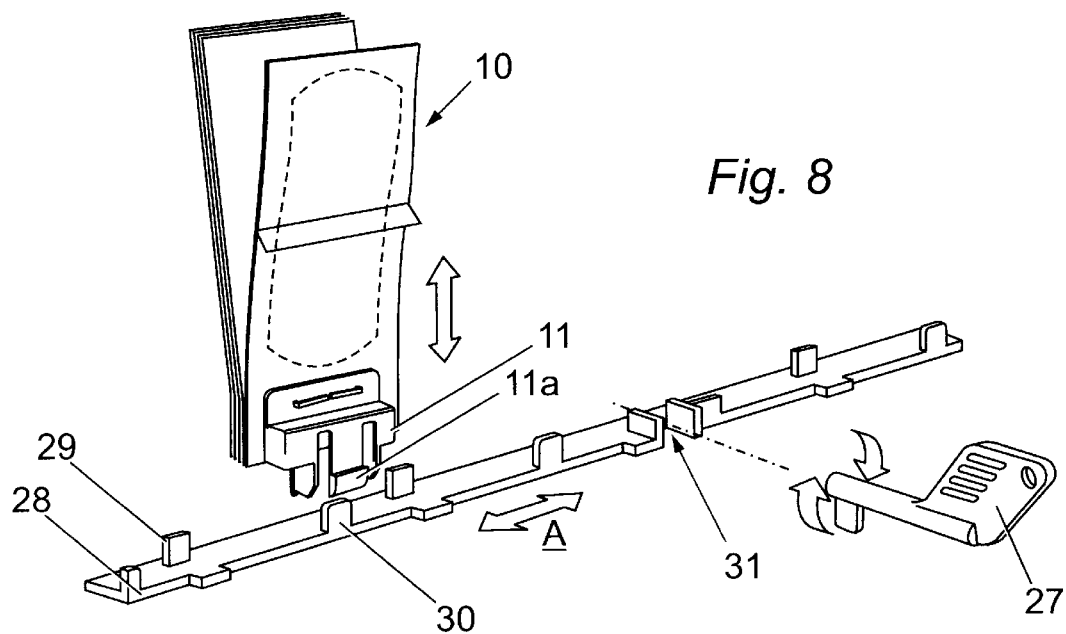
FIG. 8 illustrates the interaction of a plaster cassette with the locking bar present in the pilfer-proof plaster system of FIGS. 6 and 7.

FIG. 8 illustrates the locking bar 28 and its interaction with cassette 10. Essentially tab 30 is located behind locking lip 11a when the locking bar is in its first position. Thus, the cassette 10 is in a locked configuration since locking clip 11a cannot be depressed past lip 25 of aperture 24 (see FIG. 6) due to the presence of tab 30. If locking bar 28 is slidably displaced as shown by arrow A, tab 30 moves from behind projection 11a which can then be depressed sufficiently to pass lip 25 of aperture 24 such that cassette 10 can be lifted out of the compartment 20. Optionally projection 11a may include an indentation on its front surface which corresponds to the end of key 27 such that key 27 can conveniently be used to depress projection 11a past lip 25. Also present on locking bar 28 are spacers 29 which facilitate accurate positioning of the locking bar 28 within casing 21.

I claim:

1. A pilfer-proof device for storing individually wrapped sticking plasters, said device comprising:

a support;

at least one cassette having holding means securely attached to a plurality of wrapped plasters, said cassette being removably attached to said support by attachment means;

a locking bar having locking means to lock said cassette into a non-removable position on said support, said bar being moveable with respect to the support between a first position wherein said locking means cooperates with said cassette or said support to lock said cassette in said non-removable position and a second position wherein said locking means does not lock said cassette;

and wherein said support is further provided with means to restrict movement of the bar from the first position.

2. The device as claimed in claim 1, wherein multiple plaster cassettes are located side by side along the locking bar and are all locked in a non-removable position on said support when the locking bar is in said first position.

3. The device claimed in claim 1, wherein the attachment means of said cassette comprises a locking clip which cooperates with a corresponding lip provided on the support.

4. The device claimed in any one of claim 1, wherein the locking bar includes locking projections spaced along its length.

5. The device as claimed in claim 1 wherein said means to restrict movement of the bar from the first position comprises a keyhole which engages with a rotating key to produce displacement of the locking bar from the first position to the second position.

6. The device as claimed in claim 1 wherein said means to restrict movement of the locking bar from the first position comprises a casing provided on said support casing which protects said bar from movement due to direct human access.

7. The device as claimed in claim 1 wherein the plasters are held in said cassette by a staple.

8. The device as claimed in claim 1 wherein said plasters are sterile.

9. The device as claimed in claim 1 wherein one face of each said plasters is provided with an adhesive layer and a removable backing sheet thereon.

10. The device as claimed in claim 1, wherein said wrappers comprise at least two portions attached together and wherein one of these portions is not held by the holding means of the plaster cassette.

11. The device claimed in claim 1, wherein the cassette is provided with guiding tongues.

12. A plaster cassette to be used in a pilfer-proof device as described in claim 1, said cassette comprising holding means which securely attach a plurality of wrapped plasters, said cassette being sized and shaped to be removably attached to the support of said pilfer-proof device by attachment means, said attachment means being able to be locked in a non-removable position whilst attached to the support by a locking bar having locking means to lock said cassette in a non-removable position on said support, said bar being moveable with respect to the support between a first position wherein said locking means cooperates with said cassette to lock said cassette in a non-removable position and a second position wherein said locking means does not lock said cassette.

13. The cassette claimed in claim 12 wherein the attachment means of said cassette comprises a locking clip which cooperates with a corresponding lip provided on the support.

14. A first aid kit including a pilfer-proof plaster device as claimed in claim 1.

* * * * *

UNITED STATES PATENT AND TRADEMARK OFFICE
CERTIFICATE OF CORRECTION

PATENT NO. : 6,050,413
DATED : April 18, 2000
INVENTOR(S) : Benedetti

Page 1 of 1

It is certified that error appears in the above-identified patent and that said Letters Patent is hereby corrected as shown below:

Column 6,
Line 65: 4. The device claimed in [any one of] claim 1, wherein the Signed and Sealed this Thirty-first Day of July, 2001

Attest:

*Nicholas P. Godici*

Attesting Officer

NICHOLAS P. GODICI
*Acting Director of the United States Patent and Trademark Office*